United States Patent [19]

Asakura et al.

[11] Patent Number: 5,385,907
[45] Date of Patent: Jan. 31, 1995

[54] OINTMENTS CONTAINING FK-506 OR DERIVATIVES THEREOF

[75] Inventors: Sotoo Asakura, Kyoto; Yoshio Murakami, Kobe; Nobuto Kanagawa, Takaoka; Toshiomi Nakate, Kobe, all of Japan

[73] Assignee: Fujisawa Pharmaceutical Co., Ltd., Osaka, Japan

[21] Appl. No.: 62,330

[22] Filed: May 17, 1993

Related U.S. Application Data

[63] Continuation of Ser. No. 750,942, Aug. 28, 1991, abandoned.

[30] Foreign Application Priority Data

Sep. 4, 1990 [JP] Japan .................... 2-235177

[51] Int. Cl.⁶ .................... A61K 31/445; A61K 31/40
[52] U.S. Cl. .................... 514/291; 514/214; 514/411; 514/947; 514/969
[58] Field of Search ............... 514/214, 291, 411, 947, 514/969

[56] References Cited

U.S. PATENT DOCUMENTS

5,061,700 10/1991 Dow et al. .................... 514/169

FOREIGN PATENT DOCUMENTS

315978 5/1989 European Pat. Off. .
423714 4/1991 European Pat. Off. .

OTHER PUBLICATIONS

Chemical Abstracts 111:89968c (1989).
Chemical Abstracts 112:91786f (1990).

*Primary Examiner*—Marianne M. Cintins
*Assistant Examiner*—William R. A. Jarvis
*Attorney, Agent, or Firm*—Oblon, Spivak, McClelland, Maier & Neustadt

[57] ABSTRACT

An ointment comprising a tricyclic compound such as FK 506 substance which is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, or the like, a solubilizing and/or absorption-promoting agent and an ointment base, which is useful for treating various skin diseases.

24 Claims, No Drawings

OINTMENTS CONTAINING FK-506 OR DERIVATIVES THEREOF

This application is a continuation of application Ser. No. 07/750,942, filed on Aug. 28, 1991, now abandoned.

BACKGROUND OF THE INVENTION

1. Field of the Invention

The present invention relates to an ointment comprising a tricyclic compound which is stable and exerts excellent absorbency. The ointment according to the present invention is useful for the treatment and/or prophylaxis of inflammatory and hyperproliferative skin diseases and cutaneous manifestations of immunologically-mediated illnesses, such as, psoriasis, atopical dermatitis, contact dermatitis and further eczematous dermatitises, seborrhoeis dermatitis, Lichen planus, Pemphigus, bullous Pemphigoid, Epidermolysis bullosa, urticaria, angioedemas, vasculitides, erythemas, cutaneous eosinophilias, Lupus erythematosus, Alopecia areata, or the like; male pattern alopecia or alopecia senilis; skin diseases such as dermatomyositis, leukoderma vulgaris, ichthyosis vulgaris, photoallergic sensitivity, cutaneous T cell lymphoma, acne, or the like.

2. Prior Art

A tricyclic compound (I) and a pharmaceutically acceptable salt thereof used in this invention have been known to possess excellent pharmacological activities such as immunosuppressive activity and antimicrobial activity, thereby useful for treating and/or preventing rejection against organs or tissue transplantation, graft versus host reaction, various autoimmune diseases and infectious diseases (Japanese Laid-Open Patent Application No. 61(1986)-148181, EP-A-0323042). Particularly, FK 506 substance represented by the following formula is produced from genus Streptomyces, in particular, *Streptomyces tsukubaensis* No. 9993 (FERM BP-927). This substance is a typical compound belonging to the tricyclic compound (I).

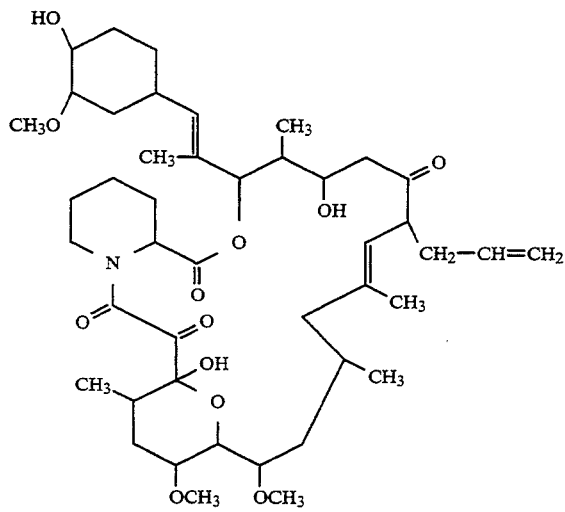

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone.

It is known that FK 506 substance is effective against inflammatory inhibition when dissolved in ethanol (EP-A-315978). The above-mentioned publication teaches that FK 506 substance can be made into a lotion, gel and cream. However, there is no disclosure in the publication about specific preparations of the lotion, gel and cream.

The present inventors have made studies about a preparation for external use comprising a compound (I) (described hereinbelow) including FK 506 substance, and found out a preparation which is excellent in stability and absorption from skin.

SUMMARY OF THE INVENTION

The present invention provides an ointment comprising a tricyclic compound represented by the following formula (I):

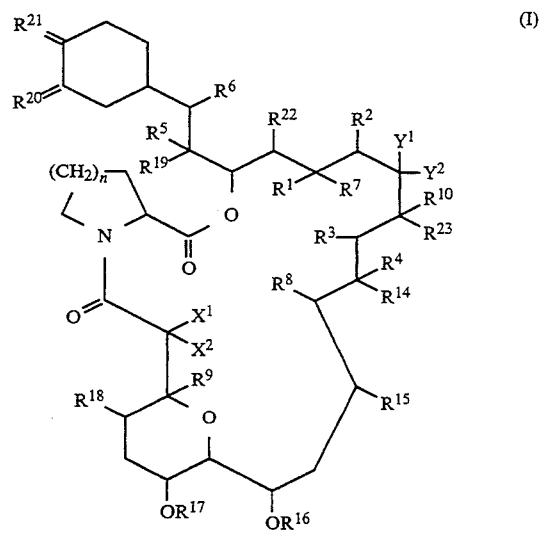

wherein each of adjacent pairs of $R^1$ and $R^2$, $R^3$ and $R^4$ or $R^5$ and $R^6$ independently is (a) two adjacent hydrogen atoms, or
(b) may form another bond formed between the carbon atoms to which they are attached, and further, $R^2$ is an alkyl group;

$R^7$ is a hydrogen atom, a hydroxy group, a protected hydroxy group or an alkoxy group, or an oxo group together with $R^1$;

$R^8$ and $R^9$ each is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

$X^1$ is a hydrogen atom or a hydroxy group;
$X^2$ is a hydrogen atom; or
$X^1$ and $X^2$ may together represent an oxo group or —CH$_2$O—;

$Y^1$ is a hydrogen atom or a hydroxy group;
$Y^2$ is a hydrogen atom; or
$Y^1$ and $Y^2$ may together represent an oxo group,

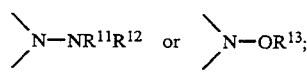

$R^{11}$ and $R^{12}$ each is independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ each is independently a hydrogen atom or an alkyl group;

$R^{20}$ and $R^{21}$ each is an oxo group or independently ($R^{20}$a and a hydrogen atom) or ($R^{21}$a and a hydrogen atom) in which $R^{20}$a and $R^{21}$a each is a hydroxy group, an alkoxy group or a group represented by the formula —OCH$_2$OCH$_2$CH$_2$OCH$_3$, or $R^{21}$a is a protected hydroxy group, or $R^{20}$a and $R^{21}$a may together represent an oxygen atom in an epoxide ring;

n is an integer of 1, 2 or 3;

in addition to their above definitions, four of $Y^1$, $Y^2$, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy, an alkoxy, benzyl and a group of the formula —CH$_2$Se(C$_6$H$_5$);

or a pharmaceutically acceptable salt thereof, a solubilizing and/or absorption-promoting agent in an amount at least sufficient to dissolve said tricyclic compound or salt thereof, and an ointment base.

PREFERRED EMBODIMENTS OF THE INVENTION

Each definition in the formula (I) will be detailed hereinbelow.

The term "lower" as used in this specification means, unless otherwise indicated, a group having 1 to 6 carbon atoms.

Preferable examples of the "alkyl groups" are a straight or branched chain aliphatic hydrocarbon residue, for example, a lower alkyl group such as methyl, ethyl, propyl, isopropyl, butyl, isobutyl, pentyl, neopentyl, hexyl and the like.

Preferable examples of the "alkenyl groups" are a straight or branched chain aliphatic hydrocarbon residue having one double-bond, for example, a lower alkenyl group such as vinyl, propenyl, butenyl, methylpropenyl, pentenyl, hexenyl and the like.

Examples of the "aryl groups" include phenyl, tolyl, xylyl, cumenyl, mesityl, naphthyl and the like.

Preferable protective groups in the "protected hydroxy groups" are 1-(lower alkylthio)(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably C$_{1-4}$ alkylthiomethyl group, most preferably methylthiomethyl group; trisubstituted silyl group such as a tri(lower)alkylsilyl (e.g., trimethylsilyl, triethylsilyl, tributylsilyl, tert-butyldimethylsilyl, tri-tert-butylsilyl, etc) or lower alkyl-diarylsilyl (e.g., methyldiphenylsilyl, ethyldiphenylsilyl, propyldiphenylsilyl, tert-butyldiphenylsilyl, etc.), more preferably tri(C$_{1-4}$)alkylsilyl group and C$_{1-4}$ alkyldiphenylsilyl group, most preferably tert-butyldimethylsilyl group and tert-butyldiphenylsilyl group; or an acyl group such as an aliphatic or aromatic acyl group derived from a carboxylic acid, sulfonic acid and carbamic acid, or an aliphatic acyl group substituted by an aromatic group.

Examples of the aliphatic acyl groups are a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group or a lower alkylcarbamoyl group having one or more substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexyicarbamoyl, etc.), protected carboxy(lower)alkylcarbamoyl group such as tri(lower)alkylsilyl(lower)alkoxycarbonyl(lower)-alkylcabamoyl group (e.g., trimethylsilylmethoxycarbonylethylcarbamoyl, trimethylsilylethoxycarbonylpropylcarbamoyl, triethylsilylethoxycarbonylpropylcarbamoyl, tertiary butyldimethylsilylethoxycarbonylpropylcarbamoyl, trimethylsilylpropoxycarbonylbutylcarbamoyl, etc.) and so on.

Examples of the aromatic acyl groups are an aroyl group optionally having one or more suitable substituents such as nitro, e.g., benzoyl, toluoyl, xyloyl, naphthoyl, nitrobenzoyl, dinitrobenzoyl, nitronaphthoyl etc.; or an arenesulfonyl group optionally having suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by aromatic group include ar(lower)alkanoyl group optionally having one or more substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are C$_{1-4}$ alkanoyl group optionally having carboxy, cyclo(C$_{5-6}$)alkoxy(C$_{1-4}$)alkanoyl group having two (C$_{1-4}$)alkyl at the cycloalkyl moiety, camphorsulfonyl group, carboxy(C$_{1-4}$)alkylcarbamoyl group, tri(C$_{1-4}$)alkylsilyl(C$_{1-4}$)alkoxycarbonyl(C$_{1-4}$)alkylcarbamoyl group, benzoyl group optionally having one or two nitro groups, benzenesulfonyl group having halogen or phenyl(C$_{1-4}$)alkanoyl group having C$_{1-4}$ alkoxy and trihalo(C$_{1-4}$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Examples of the "heterocyclic groups" in the saturated or unsaturated 5- or 6-membered nitrogen, sulfur and/or oxygen containing ring include a pyrrolyl group or a tetrahydrofuryl group.

The pharmaceutically acceptable salts of the compound (I) include conventional non-toxic and pharmaceutically acceptable salts such as the salts with inorganic or organic bases, specifically, an alkali metal salt such as sodium salt or potassium salt, an alkali earth metal salt such as calcium salt or magnesium salt, an ammonium salt or an amine salt such as triethylamine salt or N-benzyl-N-methylamine salt.

FK 506 substance is the most preferable compound belonging to the compound (I). Another preferable compounds are listed hereinbelow.

1,14-dihydroxy-12-[2-(4-hydroxy-3-methoxycyclohexyl)-1-methylvinyl]-23,25-dimethoxy-13,19,17,21,27-pentamethyl-11,28-dioxa-4-azatricyclo[22.3.1.0$^{4,9}$]octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclohexyl]-1-methylvinyl]-11,28-dioxa-4-azatricyclo[22.3.1.0$^{4,9}$]octacos-18-ene-2,3,10,16-tetraone, 17-allyl-12-[2-[4-[(-)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone, and 17-ethyl-1,14-dihydroxy-12-[2-(4-hydroxy-3-methoxycyclohexyl)-i-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (hereinafter referred to as FR 900520 substance).

The compound (I) or its salt is contained in the ointment in an amount of 0.01 to 10% (W/W), preferably 0.01 to 5% (W/W), more preferably 0.1 to 3% (W/W). In the present invention, the compound (I) is dissolved in a solubilizing and/or absorption-promoting agent.

The solubilizing and/or absorption-promoting agent used in the present invention means an agent which is capable of solubilizing the compound (I) or its salt to have a concentration of at least 0.1% (W/W) or more, and further promoting the absorption of the compound (I) or its salt from skin when the compound (I) or its salt is formulated as an ointment. In other words, the solubilizing and/or absorption-promoting agent affords solubilizing and absorbing abilities to the compound (I) or its salt. The solubilizing and/or absorption-promoting agents of the present invention include the agent possessing either one of solubilizing or absorbing abilities. As a result of various studies about the agents possessing the above two abilities, the followings are listed as the solubilizing and/or absorption-promoting agent.

lower alkanediols (ethylene glycol, propylene glycol, butylene glycol, etc.);
lower alkylene carbonates (propylene carbonate, ethylene carbonate, etc.);
alkane dicarboxylic esters (dimethyl adipate, diethyl adipate, diisopropyl adipate, diethyl pimelate, diethyl sebacate, dipropyl sebacate etc.);
higher alkane carboxylic glycerin esters (monolaurin, dilaurin, trilaurin, etc.);
higher alkene carboxylic glycerin esters (monoolein, diolein, triolein, etc.);
higher alkane carboxylic alkyl esters (isopropyl myristate, ethyl myristate, etc.);
higher unsaturated alcohols (geraniol, oleyl alcohol, etc.) and
azacycloalkanes (1-dodecylazacycloheptan-2-one, etc.).

Preferable agents among these are lower alkanediols, lower alkylene carbonates and alkane dicarboxylic esters. More preferable agents are propylene carbonate, propylene glycol and diisopropyl adipate.

The solubilizing and/or absorption-promoting agent is used in an amount at least sufficient to dissolve the compound (I) or its salt, specifically, in an amount of 1 to 300, more preferably 2 to 200 parts by weight to the compound (I). The upper limit amount of the agent is set to an amount for not destroying the desired characteristics of the ointment. According to the present invention, the amount of the solubilizing and/or absorption-promoting agent is preferably the minimum required for dissolving the compound (I) or its salt or slightly more than that in view of the absorbing ability. Specifically, propylene carbonate or propylene glycol is preferably used in an amount of 1 to 100, more preferably 2 to 50 parts by weight to the compound (I). Diisopropyl adipate is preferably used in an amount of 5 to 300, more preferably 10 to 200 parts by weight to the compound (I). The solubilizing and/or absorption-promoting agent is contained in the ointment in an amount of 1 to 30% (W/W), preferably 1 to 20% (W/W).

The solubilizing and/or absorption-promoting agent may be used singly or in combination thereof.

According to the present invention, a solution comprising the compound (I) or its salt (in the solubilizing and/or absorption-promoting agent) is formulated with an ointment base by any known method.

Examples of the ointment bases are oil and fat bases, especially, natural wax (white bees wax, carnauba wax, purified lanolin, anhydrous lanolin, etc.), petroleum wax (solid paraffin, microcrystalline wax, etc.), higher aliphatic acid glycerine ester, preferably, mono higher aliphatic acid glycerine ester (e.g., monostearin, etc.) or hydrocarbons (liquid paraffin, white petrolatum, yellow petrolatum, etc.). Preferably, these are used in combination.

The ointment of the present invention may contain, in addition to the ointment base, other additives usable for an ointment, such as perfumes, colorants, preservatives or absorption-promoting agents such as higher alkene carboxylic acid (e.g., oleic acid) or other drugs effective for skin diseases.

In view of one aspect of the present invention, there is provided a process for preparing an ointment which comprises dissolving the compound (I) or its salt in a solubilizing and/or absorption-promoting agent, compounding the resultant solution with an ointment base, stirring the resultant solution under heating and thereafter cooling the resultant solution to prepare an ointment. In this process, one or more additives optionally together with an additional amount of the solubilizing and/or absorption-promoting agent which is the same as or different from that used for dispersing the compound (I) or its salt may be generally incorporated into an ointment simultaneous with the ointment base.

The present invention includes the ointment which may contain the compound (I) or its salt partially as crystals.

The ointment of the present invention can be applied to the affected part of the skin one to four time a day.

An ointment can also be obtained when the compounds disclosed in the documents listed below are employed instead of the compound (I) or its salt of the present invention, such as EP-A-353678, Japanese Patent Application No. HEI 2(1990)-74330, PCT/GB90/01262, EP-A-413532, PCT/JP91/00314, British Patent Application No. 9012963.6, British Patent Application No. 9014136.7, British Patent Application No. 014681.2, British Patent Application No. 9014880.0, British Patent Application No. 9014881.8, British Patent Application No. 9015098.8, British Patent Application No. 9016115.9, British Patent Application No. 9016693.5, EP-A-323865, EP-A-349061, EP-A-358508, EP-A-364031, EP-A-364032, EP-A-378317, EP-A-

378320, EP-A-378321, EP-A-388153, EP-A-396399, EP-A-396400, EP-A-399579, EP-A-403242, EP-A-428365, EP-A-356399, GB 2225576 A, EP-A-402931 and EP-A-427680.

The present invention will be explained hereinbelow with reference to the Examples.

Example 1

FK 506 substance (4 g) was dissolved in propylene carbonate (20 g) at 70° C. The resultant solution was represented by solution (I). A mixture of white bees wax (26.8 g), liquid paraffin (57.6 g) and white petrolatum (291.6 g) was heated at 70° to 75° C. to make a solution, to which the solution (I) was added. The resultant solution was stirred by a homomixer (TK homomixer manufactured by Tokushu Kika Kogyo Co., Ltd., Japan) at 70° C. under 7000 rpm for 10 minutes, and thereafter, stirred under 5000 rpm for about 30 minutes to be cooled to 50° C. at room temperature. Furthermore, the resultant solution was slowly stirred by a paddle to be cooled to about 40° C. at room temperature, thereby preparing an ointment containing 1% of FK 506 substance.

Example 2

FK 506 substance (0.4 g) was dissolved in propylene carbonate (8 g) under heating. A mixture of white bees wax (32 g), liquid paraffin (68 g) and white petrolatum (291.6 g) was heated to make a solution, to which the obtained solution was added. The resultant solution was stirred by the same manner as in Example 1, thereby preparing an ointment containing 0.1% of FK 506 substance and 2% of propylene carbonate.

Example 3

FK 506 substance (4 g) was dissolved under heating in propylene glycol (20 g), thereby preparing by the same manner as in Example 1, an ointment containing 1% of FK 506 substance and 5% of propylene glycol.

Example 4

FK 506 substance (0.4 g) was dissolved in propylene carbonate (20 g) under heating. A mixture of solid paraffin (12 g), liquid paraffin (47.6 g) and white petrolatum (320 g) was heated to make a solution, to which the obtained solution was added. The resultant solution was stirred by the same manner as in Example 1, thereby preparing an ointment containing 0.1% of FK 506 substance and 5% of propylene carbonate.

Example 5

FK 506 substance (0.1 g) was dissolved in diethyl sebacate (20 g) under heating. A mixture of white bees wax (3.5 g), solid paraffin (3 g) and white petrolatum (73.4 g) was heated to make a solution, to which the obtained solution was added. The resultant solution was stirred by the same manner as in Example 1, thereby preparing an ointment containing 0.1% of FK 506 substance and 20% of diethyl sebacate.

Example 6

FK 506 substance (0.1 g) was dissolved in diisopropyl adipate (20 g) under heating. A mixture of microcrystalline wax (6 g) and white petrolatum (73.9 g) was heated to make a solution, to which the obtained solution was added. The resultant solution was stirred by the same manner as in Example 1, thereby preparing an ointment containing 0.1% of FK 506 substance and 20% of diisopropyl adipate.

Example 7

FK 506 substance (0.1 g) was dissolved in monolaurin (10 g) under heating. A mixture of white bees wax (3.5 g), solid paraffin (3 g) and white petrolatum (83.4 g) was heated to make a solution, to which the obtained solution was added. The resultant solution was stirred by the same manner as in Example 1, thereby preparing an ointment containing 0.1% of FK 506 substance and 10% of monolaurin.

Example 8

An ointment containing 0.1% of FK 506 substance and 10 of oleyl alcohol was prepared by the same manner as in Example 7, except that oleyl alcohol (10 g) was used instead of monolaurin.

Example 9

An ointment containing 0.1% of FK 506 substance and 10% of monoolein was prepared by the same manner as in Example 7, except that monoolein (10 g) was used instead of monolautin.

Example 10

An ointment containing 0.1% of FK 506 substance and 10% of Azone was prepared by the same manner as in Example 7, except that 1-dodecylazacycloheptan-2-one [Azone ® manufactured by Nelson Research and Development] (10 g) was used instead of monolaurin.

Reference Example 1 (Control)

FK 506 substance (0.1 g), white bees wax (8.6 g), liquid paraffin (18.4 g) and white petrolatum (72.9 g) were well mixed in a mortar for about 30 minutes, thereby preparing an ointment containing 0.1% FK 506 substance.

Example 11

FK 506 substance (4 g) was dissolved in propylene carbonate (20 g) at 70° C. The resultant solution was represented by solution (I). A mixture of white bees wax (27.6 g), liquid paraffin (57.6 g) and white petrolatum (290.8 g) was heated at 70 to 75° C. to make a solution, to which the solution (I) was added. The resultant solution was stirred by a homomixer (TK homomixer manufactured by Tokushu Kika Kogyo Co., Ltd.) at 70° C. under 7000 rpm for about 10 minutes, and thereafter, stirred under 5000 rpm for about 30 minutes to be cooled to 50° C. at room temperature. Furthermore, the resultant solution was slowly stirred by a paddle to be cooled to about 40° C. at room temperature, thereby preparing an ointment containing 1% of FK 506 substance.

Example 12

FK 506 substance (4 g) was dissolved in propylene glycol (20 g) under heating, thereby preparing by the same manner as in Example 11 an ointment containing 1% of FK 506 substance and 5% of propylene glycol.

Example 13

FK 506 substance (0.4 g) was dissolved in propylene glycol (8 g) under heating. A mixture of white bees wax (32 g), liquid paraffin (68 g) and white petrolatum (291.6 g) was heated to make a solution, to which the obtained solution was added. The resultant solution was stirred by the same manner as in Example 11, thereby preparing an ointment containing 0.1% of FK 506 substance and 2% of propylene glycol.

Example 14

FK 506 substance (4 g) was dissolved in propylene carbonate (20 g) at 70° C. The resultant solution was represented by (I) solution. A mixture of monolaurin (20 g), white bees wax (26.8 g), liquid paraffin (37.6 g) and white petrolatum (291.6 g) was heated at 70° to 75° C. to make a solution, to which the (I) solution was added. The resultant solution was stirred by a homomixer at 70° C. under 7000 rpm for 10 minutes, and thereafter, stirred under 5000 rpm for about 30 minutes to be cooled to 50° C. at room temperature. Furthermore, the resultant solution was slowly stirred by a paddle to be cooled to about 40° C. at room temperature, thereby preparing an ointment containing 1% of FK 506 substance.

Example 15

An ointment containing 1% of FK 506 substance and 5% of oleyl alcohol was prepared by the same manner as in Example 14, except that oleyl alcohol (20 g) was used instead of monolaurin.

Example 16

An ointment containing 1% of FK 506 substance and 5% of oleic acid was prepared by the same manner as in Example 14, except that oleic acid (20 g) was used instead of monolaurin.

Example 17

FK 506 substance (8 g) was dissolved in propylene carbonate (40 g) under heating. A mixture of white bees wax (25.2 g), liquid paraffin (35.2 g) and white petrolatum (291.6 g) was heated to make a solution, to which the obtained solution was added. The resultant solution was stirred by the same manner as in Example 1, thereby preparing an ointment containing 2% of FK 506 substance.

Example 18

FK 506 substance (0.1 g) was dissolved in propylene glycol (2 g) under heating. A mixture of isopropyl myristate (10 g), white bees wax (3.5 g), liquid paraffin (5 g), solid paraffin (3 g) and white petrolatum (76.4 g) was heated to make a solution, to which the obtained solution was added. The resultant solution was stirred by the same manner as in Example 1, thereby preparing an ointment containing 0.1% of FK 506 substance.

Example 19

FK 506 substance (0.4 g) was dissolved in propylene carbonate (20 g) under heating. A mixture of white bees wax (28 g), liquid paraffin (60 g) and white petrolatum (291.6 g) was heated to make a solution, to which the obtained solution was added. The resultant solution was stirred by the same manner as in Example 1, thereby preparing an ointment containing 0.1% of FK 506 substance and 5% of propylene carbonate.

Example 20

FK 506 substance (1 g) was dissolved in propylene carbonate (5 g) under heating. A mixture of diisopropyl adipate (10 g), white bees wax (6.7 g), liquid paraffin (5 g), microcrystalline wax (1 g) and white petrolatum (72.3 g) was heated to make a solution, to which the obtained solution was added. The resultant solution was stirred by the same manner as in Example 1, thereby preparing an ointment containing 1% of FK 506 substance.

Example 21

FK 506 substance (1 g) was dissolved in propylene carbonate (5 g) under heating. A mixture of diisopropyl adipate (10 g), white bees wax (3.5 g), liquid paraffin (1 g), solid paraffin (3 g) and white petrolatum (76.5 g) was heated to make a solution, to which the obtained solution was added. The resultant solution was stirred by the same manner as in Example 1, thereby preparing an ointment containing 1% of FK 506 substance.

Example 22

FK 506 substance (0.3 g) was dissolved in propylene carbonate (5 g) under heating. A mixture of diisopropyl adipate (10 g), white bees wax (3.5 g), liquid paraffin (1 g), solid paraffin (3 g) and white petrolatum (77.2 g) was heated to make a solution, to which the obtained solution was added. The resultant solution was stirred by the same manner as in Example 1, thereby preparing an ointment containing 0.3% of FK 506 substance.

Example 23

FK 506 substance (0.1 g) was dissolved in propylene carbonate (5 g) under heating. A mixture of diisopropyl adipate (10 g), white bees wax (3.5 g), liquid paraffin (1 g), solid paraffin (3 g) and white petrolatum (77.4 g) was heated to make a solution, to which the obtained solution was added. The resultant solution was stirred by the same manner as in Example 1, thereby preparing an ointment containing 0.1% of FK 506 substance.

Example 24

FR 900520 substance (1 g) was dissolved in propylene carbonate (5 g) under heating. A mixture of diisopropyl adipate (10 g), white bees wax (6.7 g), liquid paraffin (5 g), microcrystalline wax (1 g) and white petrolatum (72.3 g) was heated to make a solution, to which the obtained solution was added. The resultant solution was stirred by the same manner as in Example 1, thereby preparing an ointment containing 1% of FR 900520 substance.

Example 25

FR 900520 substance (0.3 g) was dissolved in propylene carbonate (5 g) under heating. A mixture of diisopropyl adipate (10 g), white bees wax (3.5 g), liquid paraffin (1 g), solid paraffin (3 g) and white petrolatum (77.2 g) was heated to make a solution, to which the obtained solution was added. The resultant solution was stirred by the same manner as in Example 1, thereby preparing an ointment containing 0.3% of FR 900520 substance.

Example 26

FK 506 substance (2.5 g) was dissolved in propylene carbonate (12.5 g) under heating. A mixture of diisopropyl adipate (25 g), liquid paraffin (2.5 g), solid paraffin (11.25 g), purified lanolin (5 g) and white petrolatum (191.25 g) was heated to make a solution, to which the obtained solution was added. The resultant solution was stirred by the same manner as in Example 1, thereby preparing an ointment containing 1% of FK 506 substance.

Example 27

FK 506 substance (2.5 g) was dissolved in propylene carbonate (12.5 g) under heating. A mixture of diisopropyl adipate (25 g), liquid paraffin (2.5 g), solid paraffin (5 g), glycerine monostearate (2.5 g) and white petrolatum (200 g) was heated to make a solution, to which the obtained solution was added. The resultant solution was stirred by the same manner as in Example 1, thereby preparing an ointment containing 1% of FK 506 substance.

Example 28

FK 506 substance (2.5 g) was dissolved in propylene carbonate (12.5 g) under heating. A mixture of diisopropyl adipate (25 g), liquid paraffin (2.5 g), solid paraffin (7.5 g), white bees wax (1.25 g) and white petrolatum (198.75 g) was heated to make a solution, to which the obtained solution was added. The resultant solution was stirred by the same manner as in Example 1, thereby preparing an ointment containing 1% of FK 506 substance.

Explained next are pharmaceutical tests and stability tests regarding the ointment of the present invention.

Test 1 (In vivo cutaneous absorption test)

An abdominal part of rats (male, SD rat, 7-week old) was depilated by electric hair clippers and depilatory cream one day before the test. On the test day, the rat was fixed on a fixed stand at a dorsal position for applying a sample (ointment) in an amount of about 100 mg to the area of 10 cm² of the depilated skin (4×2.5 cm) by a microspatula. Immediately after and 8 hours after the application, the sample remaining on the skin was scraped off by the microspatula. The surface of the skin was wiped off by four absorbent cottons moistened with ethanol. The collected substance was put into a centrifuged tube, to which 20 ml of solution (n-hexane/ethanol=1/1) was added. The tube was shaken. The extracted supernatant fluid was poured into HPLC having the following conditions to quantify the amount of FK 506 substance. The measurement was conducted three times.

HPLC Conditions
Column: TSK-gel OH-120 25 cm×4.6 mmΦ
Mobile phase: n-hexane/anhydrous ethanol =4/1
Detector: UV 214 nm

| Test Preparation | Results Cutaneous Absorbance (%) |
|---|---|
| Example 13 | 17.3 |
| Example 2 | 8.5 |
| Reference Example 1 | 0.8 |

Test 2 (Anti-inflammatory test)

A 3% croton oil—diethyl ether solution (20 μl) was applied to the back of both auricles of a mouse to cause reaction (while diethyl ether (20 μl) was similarly applied to cause spontaneous swelling). After six hours, the thickness of each auricle was measured. A degree of swelling was obtained by subtracting the thickness of each auricle before the reaction from that after the reaction. This degree is represented as an index of the strength of inflammatory edema.

A test preparation (20 μl) was applied to the back of both auricles three hours before the application of the croton oil. The applied preparation was wiped off with 70% ethanol immediately before the application of the croton oil.

| Test Preparation | Inhibition Rate (%) |
|---|---|
| Example 11 | 66.8 |
| Example 12 | 54.7 |
| 1% FK 506 substance ethanolic solution (for comparison) | 14.4 |

Test 3 (Stability test)

An ointment (5 g) prepared in Example 19 was filled in phenol coat tube and kept at 40° C. for a predetermined period of time. Thereafter, the residual rate of FK 506 substance was measured.

| | Residual rate (%) |
|---|---|
| After 1 month | 97.4 |
| After 2 months | 96.7 |
| After 3 months | 94.0 |

Skin irritation tests were conducted by applying ointments prepared in Examples 1 and 3 to guinea pig. The result shows that no skin irritation was observed.

According to the present invention, the use of a solubilizing and/or absorption-promoting agent can provide a stable ointment which is excellent in absorption of effective compositions. The ointment provided by the present invention is useful for treating and preventing various skin diseases.

What is claimed is:

1. An ointment consisting essentially of a tricyclic compound represented by the following formula (I):

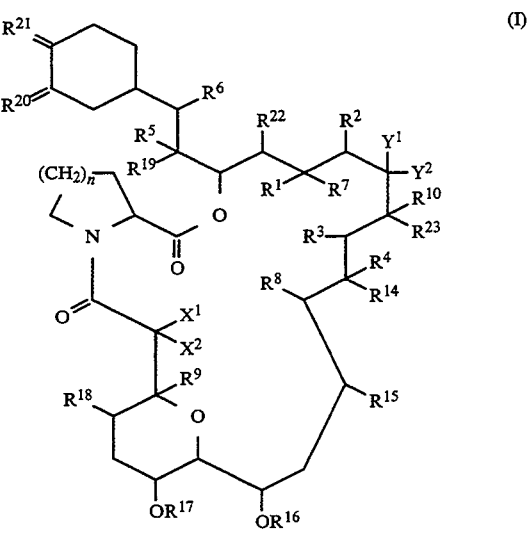

wherein each of adjacent pairs of $R^1$ and $R^2$, $R^3$ and $R^4$ or $R^5$ and $R^6$ independently is
 (a) two adjacent hydrogen atoms, or
 (b) may form another bond formed between the carbon atoms to which they are attached,
 and further, $R^2$ is an alkyl group;
$R^7$ is a hydrogen atom, a hydroxy group, a protected hydroxy group or an alkoxy group, or an oxo group together with $R^1$; $R^8$ and $R^9$ each is independently a hydrogen atom or a hydroxy group;

$R^{10}$ is a hydrogen atom, and alkyl group, an alkyl group substituted by one or more hydroxy groups, an alkenyl group, an alkenyl group substituted by one or more hydroxy groups or an alkyl group substituted by an oxo group;

$X^1$ is a hydrogen atom or a hydroxy group;

$X^2$ is a hydrogen atom; or $X^1$ and $X^2$ may together represent an oxo group or —CH$_2$O—;

$Y^1$ is a hydrogen atom or a hydroxy group;

$Y^2$ is a hydrogen atom; or $Y^1$ and $Y^2$ may together represent an oxo group,

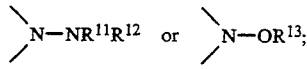

$R^{11}$ and $R^{12}$ each is independently a hydrogen atom, an alkyl group, an aryl group or a tosyl group; $R^{13}$, $R^{14}$, $R^{15}$, $R^{16}$, $R^{17}$, $R^{18}$, $R^{19}$, $R^{22}$ and $R^{23}$ each is independently a hydrogen atom or an alkyl group;

$R^{20}$ and $R^{21}$ each is an oxo group or independently ($R^{20}$a and a hydrogen atom) or ($R^{21}$a and a hydrogen atom) in which $R^{20}$a and $R^{21}$a each is a hydroxy group, an alkoxy group or a group represented by the formula —OCH$_2$OCH$_2$CH$_2$OCH$_3$, or $R^{21}$a is a protected hydroxy group, or $R^2$a and $R^2$a may together represent an oxygen atom in an epoxide ring;

n is an integer of 1, 2 or 3;

in addition to their above definitions, four of $Y^1$, $Y^2$, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy, an alkoxy, benzyl and a group of the formula —CH$_2$Se(C$_6$H$_5$);

or a pharmaceutically acceptable salt thereof, a solubilizing and/or absorption-promoting agent selected from the group consisting of a lower alkanediol, a lower alkylene carbonate, an alkane dicarboxylic ester, a higher alkane carboxylic glycerin ester, a higher alkene carboxylic glycerin ester, a higher alkane carboxylic alkyl ester, a higher unsaturated alcohol and an azacycloalkane, and an ointment based selected from the group consisting of oil and fat bases;

in which the tricyclic compound (I) or a pharmaceutically acceptable salt thereof is contained therein in an amount of about 0.01 to 10% (w/w), and the solubilizing and/or absorption-promoting agent is contained therein in an amount of about 1 to 30% (w/w), where optionally is present one or more of the following ingredients selected from the group consisting of colorants, preservatives, and higher alkene carboxylic acids.

2. An ointment as claimed in claim 1 in which the solubilizing and/or absorption-promoting agent is a lower alkanediol, a lower alkylene carbonate or an alkane dicarboxylic ester.

3. An ointment as claimed in claim 1 in which the tricyclic compound (I) is the one wherein each of adjacent pairs of $R^3$ and $R^4$ or $R^5$ and $R^6$ independently may form another bond formed between the carbon atoms to which they are attached, $R^8$ and $R^{23}$ each is independently a hydrogen atom;

$R^9$ is a hydroxy group;

$R^{10}$ is methyl, ethyl, propyl or allyl;

$X^1$ is a hydrogen atom;

$X^2$ is a hydrogen atom; or $X^1$ and $X^2$ may together represent an oxo group;

$Y^1$ and $Y^2$ may together represent an oxo group;

$R^{14}$, $R^{15}$, $R^{16}$, $R^{17}$, $R^{18}$, $R^{19}$ and $R^{22}$ each is independently methyl;

$R^{20}$ and $R^{21}$ independently are ($R^{20}$a and a hydrogen atom) or ($R^{21}$a and a hydrogen atom) in which $R^{20}$a and $R^{21}$a each is a hydroxy group or an alkoxy group or $R^{21}$a is a protected hydroxy group; and n is an integer of 1 or 2.

4. An ointment as claimed in claim 3 in which the tricyclic compound (I) is the one wherein $R^7$ is a hydrogen atom, a hydroxy group or a protected hydroxy group;

$X^1$ and $X^2$ may together represent an oxo group;

$R^{20}$a is methoxy; and $R^{21}$a is a hydroxy or protected hydroxy group.

5. An ointment as claimed in claim 4 in which the tricyclic compound (I) is 17-allyl-1,14-dihydroxy-12-[2--(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

6. An ointment as claimed in claim 4 in which the tricyclic compound (I) is 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

7. An ointment of claim 1, wherein at least one of said ingredients selected from the group consisting of perfumes, colorants, preservatives, and higher alkene carboxylic acids is present.

8. An ointment as claimed in claim 2 in which the tricyclic compound (I) is the one wherein each of adjacent pairs of $R^3$ and $R^4$ or $R^5$ and $R^6$ independently may form another bond formed between the carbon atoms to which they are attached, $R^8$ and $R^{23}$ each is independently a hydrogen atom;

$R^9$ is a hydroxy group;

$R^{10}$ is methyl, ethyl, propyl or allyl;

$X^1$ is a hydrogen atom;

$X^2$ is a hydrogen atom; or $X^1$ and $X^2$ may together represent an oxo group;

$Y^1$ and $Y^2$ may together represent an oxo group;

$R^{14}$, $R^{15}$, $R^{16}$, $R^{17}$, $R^{18}$, $R^{19}$ and $R^{22}$ each is independently methyl;

$R^{20}$ and $R^{21}$ independently are ($R^{20}$a and a hydrogen atom) or ($R^{21}$a and a hydrogen atom) in which $R^{20}$a and $R^{21}$a each is a hydroxy group or an alkoxy group or $R^{21}$a is a protected hydroxy group; and n is an integer of 1 or 2.

9. An ointment as claimed in claim 8 in which the tricyclic compound (I) is the one wherein $R^7$ is a hydrogen atom, a hydroxy group or a protected hydroxy group;

$X^1$ and $X^2$ may together represent an oxo group;

$R^{20}$a is a methoxy; and $R^{21}$a is a hydroxy or protected hydroxy group.

10. An ointment as claimed in claim 9 in which the tricyclic compound (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

11. An ointment as claimed in claim 9 in which the tricyclic compound (I) is 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

12. An ointment as claimed in claim 1 consisting of a tricyclic compound represented by the following formula (I):

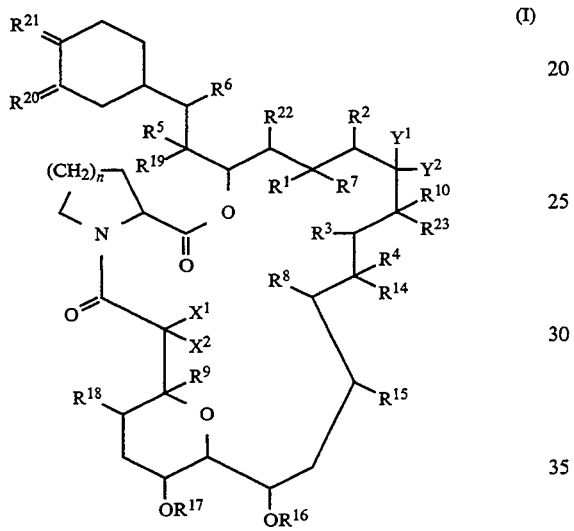

wherein each of adjacent pairs of $R^1$ and $R^2$, $R^3$ and $R^4$ or $R^5$ and $R^6$ independently is
 (a) two adjacent hydrogen atoms, or
 (b) may form another bond formed between the carbon atoms to which they are attached, and further, $R^2$ is an alkyl group;

$R^7$ is a hydrogen atom, a hydroxy group, a protected hydroxy group or an alkoxy group, or an oxo group together with $R^1$;

$R^8$ and $R^9$ each is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

$X^1$ is a hydrogen atom or a hydroxy group;

$X^2$ is a hydrogen atom; or $X^1$ and $X^2$ may together represent an oxo group or —CH$_2$O—;

$Y^1$ is a hydrogen atom or a hydroxy group;

$Y^2$ is a hydrogen atom; or $Y^1$ and $Y^2$ may together represent an oxo group,

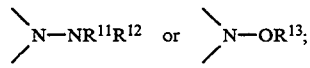

$R^{11}$ and $R^{12}$ each is independently a hydrogen atom, an alkyl group, an aryl group or a tosyl group;

$R^{13}$ $R^{14}$, $R^{15}$, $R^{16}$, $R^{17}$, $R^{18}$, $R^{19}$, $R^{22}$ and $R^{23}$ each is independently a hydrogen atom or an alkyl group;

$R^{20}$ and $R^{21}$ each is an oxo group or independently ($R^{20}$a and a hydrogen atom) or ($R^{21}$a and a hydrogen atom) in which $R^{20}$a and $R^{21}$a each is a hydroxy group, an alkoxy group or a group represented by the formula —OCH$_2$OCH$_2$CH$_2$OCH$_3$, or $R^{21}$a is a protected hydroxy group, or $R^{20}$a and $R^{21}$a may together represent an oxygen atom in an epoxide ring;

n is an integer of 1, 2 or 3;

in addition to their above definitions, four of $Y^1$, $Y^2$, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy, an alkoxy, benzyl and a group of the formula —CH$_2$Se(C$_6$H$_5$); or a pharmaceutically acceptable salt thereof, a solubilizing and/or absorption-promoting agent selected from the group consisting of a lower alkanediol, a lower alkylene carbonate, an alkane dicarboxylic ester, a higher alkane carboxylic glycerin ester, a higher alkene carboxylic glycerin ester, a higher alkane carboxylic alkyl ester, a higher unsaturated alcohol and an azacycloalkane, and an ointment base selected from the group consisting of oil and fat bases;

in which the tricyclic compound (I) or a pharmaceutically acceptable salt thereof is contained therein in an amount of about 0.01 to 10% (w/w), and the solubilizing and/or absorption-promoting agent is contained therein in an amount of about 1 to 30% (w/w).

13. An ointment as claimed in claim 1, wherein said oil and fat bases are selected from the group consisting of natural waxes, petroleum waxes, higher aliphatic acid glycerin esters, hydrocarbons, and mixtures thereof.

14. An ointment as claimed in claim 12, wherein said oil and fat bases are selected from the group consisting of natural waxes, petroleum waxes, higher aliphatic acid glycerin esters, hydrocarbons, and mixtures thereof.

15. An ointment as claimed in claim 1, wherein said ointment base consists of white petrolatum, solid paraffin, liquid paraffin and white beeswax and wherein said solubilizing and/or absorption-promoting agent is selected from the group consisting of propylene carbonate alone or in combination with diisopropyl adipate.

16. An ointment as claimed in claim 12, wherein said ointment base consists of white petrolatum, solid paraffin, liquid paraffin and white beeswax and wherein said solubilizing and/or absorption-promoting agent is selected from the group consisting of propylene carbonate alone or in combination with diisopropyl adipate.

17. An ointment as claimed in claim 1, in which the tricyclic compound represented by formula (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

18. The ointment as claimed in claim 17, wherein said solubilizing and/or absorption-promoting agent is a lower alkylene carbonate.

19. The ointment as claimed in claim 18, wherein said lower alkylene carbonate is propylene carbonate.

20. An ointment as claimed in claim 12, in which the tricyclic compound represented by formula (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

21. The ointment as claimed in claim 20, wherein said solubilizing and/or absorption-promoting agent is a lower alkylene carbonate.

22. The ointment as claimed in claim 21, wherein said lower alkylene carbonate is propylene carbonate.

23. An ointment as claimed in claim 15, wherein said solubilizing and/or absorption-promoting agent is propylene carbonate and wherein said tricyclic compound represented by formula (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

24. An ointment as claimed in claim 16, wherein said solubilizing and/or absorption-promoting agent is propylene carbonate and wherein said tricyclic compound represented by formula (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

* * * * *